US012584906B2

(12) United States Patent
Matsunaga et al.

(10) Patent No.: US 12,584,906 B2
(45) Date of Patent: Mar. 24, 2026

(54) COATING AGENT FOR INDUCING DIFFERENTIATION OF PLURIPOTENT STEM CELLS INTO BRAIN MICROVASCULAR ENDOTHELIUM-LIKE CELLS AND USE THEREOF

(71) Applicant: PUBLIC UNIVERSITY CORPORATION NAGOYA CITY UNIVERSITY, Nagoya (JP)

(72) Inventors: Tamihide Matsunaga, Nagoya (JP); Tadahiro Hashita, Nagoya (JP); Hiromasa Aoki, Nagoya (JP); Misaki Yamashita, Nagoya (JP)

(73) Assignee: PUBLIC UNIVERSITY CORPORATION NAGOYA CITY UNIVERSITY, Nagoya (JP)

( * ) Notice: Subject to any disclaimer, the term of this patent is extended or adjusted under 35 U.S.C. 154(b) by 770 days.

(21) Appl. No.: 17/798,206

(22) PCT Filed: Feb. 9, 2021

(86) PCT No.: PCT/JP2021/004762
§ 371 (c)(1),
(2) Date: Aug. 8, 2022

(87) PCT Pub. No.: WO2021/161991
PCT Pub. Date: Aug. 19, 2021

(65) Prior Publication Data
US 2023/0084457 A1 Mar. 16, 2023

(30) Foreign Application Priority Data
Feb. 10, 2020 (JP) ................................. 2020-021031

(51) Int. Cl.
*G01N 33/50* (2006.01)
*C12N 5/071* (2010.01)

(52) U.S. Cl.
CPC ....... *G01N 33/5082* (2013.01); *C12N 5/0692* (2013.01); *C12N 2506/45* (2013.01); *C12N 2533/52* (2013.01); *C12N 2533/54* (2013.01)

(58) Field of Classification Search
CPC .... C12N 5/0696; C12N 5/0692; C12N 5/069; C12N 2533/54; C12N 2533/52; C12N 2501/115; C12N 2533/90; C12N 2500/99; C12N 2506/45; C12N 2537/10; C12M 23/10; C12M 23/20; G01N 33/5064; G01N 33/5082
See application file for complete search history.

(56) References Cited

U.S. PATENT DOCUMENTS

| | | |
|---|---|---|
| 5,260,210 A | 11/1993 | Rubin et al. |
| 2016/0186146 A1 | 6/2016 | Thomson et al. |
| 2017/0313976 A1 | 11/2017 | Kuwahara et al. |
| 2018/0208893 A1 | 7/2018 | Nakahata et al. |
| 2018/0273906 A1 | 9/2018 | Ashraf |
| 2018/0334656 A1 | 11/2018 | Suemori et al. |
| 2019/0093084 A1 | 3/2019 | Shusta et al. |
| 2019/0153391 A1 | 5/2019 | Ochi et al. |

FOREIGN PATENT DOCUMENTS

| | | |
|---|---|---|
| CN | 106715685 A | 5/2017 |
| CN | 110709509 A | 1/2020 |
| JP | 2015-159785 A | 9/2015 |
| JP | 2018-506963 A | 3/2018 |
| JP | 2018-131426 A | 8/2018 |
| JP | 2019-201631 A | 11/2019 |
| WO | WO 2011/159572 A2 | 12/2011 |
| WO | WO 2016/063985 A1 | 4/2016 |
| WO | WO 2017/014165 A1 | 1/2017 |
| WO | WO 2017/082220 A1 | 5/2017 |
| WO | WO 2018/149985 A1 | 8/2018 |
| WO | WO 2019/208736 A1 | 10/2019 |
| WO | WO 2020/252477 A1 | 12/2020 |

OTHER PUBLICATIONS

Yap et al. In Vivo Generation of Post-infarct Human Cardiac Muscle by Laminin-Promoted Cardiovascular Progenitors. Cell Reports (Mar. 2019), 26, 3231-3245 and Star Methods. (Year: 2019).*
Aoki et al. Laminin 221 fragment is suitable for the differentiation of human induced pluripotent stem cells into brain microvascular endothelial-like cells with robust barrier . Fluid Barriers CNS (Mar. 2020), 17:25, 11 pages. (Year: 2020).*
Jamieson et al. Role of iPSC-derived pericytes on barrier function of iPSC-derived brain microvascular endothelial cells in 2D and 3D. Fluids Barrier CNS (Jun. 2019), 16:15, 16 pages. (Year: 2019).*
Nishishita et al. An effective freezing/thawing method for human pluripotent stem cells cultured in chemically-defined and feeder-free conditions. Am J Stem Cells (2015), 4(1), 38-49. (Year: 2015).*
Hollmann et al., "Accelerated differentiation of human induced pluripotent stem cells to blood-brain barrier endothelial cells", Fluids Barriers CNS (2017) 14:9, p. 1-13.
International Search Report, issued in PCT/JP2021/004762, PCT/ISA/210, dated Apr. 6, 2021.
Patel et al., "Growth-factor reduced Matrigel source influences stem cell derived brain microvascular endothelial cell barrier properties", Fluids Barriers CNS (2016) 13:6, p. 1-7.
Written Opinion of the International Searching Authority, issued in PCT/JP2021/004762, PCT/ISA/237, dated Apr. 6, 2021.

(Continued)

*Primary Examiner* — Sean C. Barron
(74) *Attorney, Agent, or Firm* — Birch, Stewart, Kolasch & Birch, LLP

(57) ABSTRACT

Provided is a technology allowing for stable supply of brain microvascular endothelium-like cells. This coating agent for inducing differentiation of pluripotent stem cells into brain microvascular endothelium-like cells contains at least one component of a Laminin-221 fragment or an N-terminal Vitronectin.

4 Claims, 7 Drawing Sheets
Specification includes a Sequence Listing.

(56)     References Cited

OTHER PUBLICATIONS

Japanese Office Action for Japanese Application No. 2022-500420, dated Jan. 28, 2025, with an English translation.

Chinese Office Action and Search Report for Chinese Application No. 202180013715.9, dated Sep. 13, 2023, with English translation.

Extended European Search Report for European Application No. 21754115.0, dated Mar. 20, 2024.

Qian et al., "Directed differentiation of human pluripotent stem cells to blood-brain barrier endothelial cells," Science Advances, vol. 3, Nov. 8, 2017, pp. 1-12.

"Safety Data Sheet," Nippi, Inc., Feb. 21, 2018, XP093345116, pp. 1-5.

European Communication pursuant to Article 94(3) EPC for European Application No. 21 754 115.0, dated Dec. 19, 2025.

* cited by examiner

Days elapsed after seeding

COATING AGENT FOR INDUCING DIFFERENTIATION OF PLURIPOTENT STEM CELLS INTO BRAIN MICROVASCULAR ENDOTHELIUM-LIKE CELLS AND USE THEREOF

TECHNICAL FIELD

The present disclosure relates to a coating agent for inducing differentiation of pluripotent stem cells into brain microvascular endothelium-like cells. The present application is based on Japanese Patent Application No. 2020-021031, filed on Feb. 10, 2020, the contents of which are herein incorporated by reference.

BACKGROUND ART

Brain microvascular endothelial cells (BMECs), one type of cells constituting the blood-brain barrier (BBB), inhibit non-specific entry of substances into the brain parenchyma by strong intercellular adhesion and expression of efflux transporters. In drug discovery, this strong barrier function inhibits transfer of a drug candidate to the brain parenchyma (nerve) side, so that drug development may be discontinued. For this reason, a screening model capable of evaluating pharmacokinetics in human BBB has been desired, and pluripotent stem cells have been induced and differentiated into brain microvascular endothelium-like cells (iBMECs) (e.g., PTL 1).

CITATION LIST

Patent Literature

[PTL 1] WO 2019/208736 A

SUMMARY OF INVENTION

Technical Problem

In PTL 1, human induced pluripotent stem cells (iPS cells) are induced and differentiated into iBMECs while cultured using a culture dish coated with Matrigel. However, Matrigel is characterized by solidification with increasing temperature, and requires complicated manipulations for coating, so that it is difficult to maintain reproducibility. In addition, since Matrigel is produced from mouse granulomas, the differentiation efficiency of iBMECs varies due to differences in the manufacturer and production lot of Matrigel. For this reason, the present inventors have conducted intensive research, and have arrived at an invention of technology allowing for stable supply of iBMECs.

Solution to Problem

The present invention has been made to solve the above-described problems, and can be implemented as the following items.

(1) An aspect of the present invention provides a coating agent for inducing differentiation of pluripotent stem cells into brain microvascular endothelium-like cells. The coating agent according to this item contains at least one component of a Laminin-221 fragment or an N-terminal Vitronectin. The coating agent according to this item makes it possible to suppress a decrease in reproducibility upon induction of differentiation of pluripotent stem cells into brain microvascular endothelium-like cells, and to suppress variation in differentiation efficiency, so that the brain microvascular endothelium-like cells can be stably supplied.

(2) The coating agent according to the above item may contain the component in an amount of 0.01 nmol/L or more and 10 mmol/L or less. The coating agent according to this item makes it possible to suppress a decrease in differentiation efficiency more potently.

(3) Another aspect of the present invention provides a differentiation induction kit. The differentiation induction kit according to this item includes the coating agent and cells. The differentiation induction kit according to this item makes it possible to easily induce differentiation of pluripotent stem cells into brain microvascular endothelium-like cells.

(4) The present invention can also be implemented as use of a coating agent for inducing differentiation of pluripotent stem cells into brain microvascular endothelium-like cells, the coating agent comprising at least one component of a Laminin-221 fragment or an N-terminal Vitronectin.

(5) Another aspect of the present invention provides a culture dish comprising a coating layer coated with a coating agent for inducing differentiation of pluripotent stem cells into brain microvascular endothelium-like cells. The coating agent for the culture dish according to this item contains at least one component of a Laminin-221 fragment or an N-terminal Vitronectin. The culture dish according to this item makes it possible to suppress a decrease in reproducibility upon induction of differentiation of pluripotent stem cells into brain microvascular endothelium-like cells, and to suppress variation in differentiation efficiency, so that the brain microvascular endothelium-like cells can be stably supplied.

(6) The culture dish according to the above item may comprise the component in an amount of 1 ng or more and 1 mg or less per cm' of coating area of the coating layer. The coating agent according to this item makes it possible to suppress a decrease in differentiation efficiency more potently.

(7) Another aspect of the present invention provides a method of producing brain microvascular endothelium-like cells by inducing differentiation of pluripotent stem cells. The method of producing brain microvascular endothelium-like cells according to this item comprises a step of culturing the pluripotent stem cells while using at least one component of a Laminin-221 fragment or an N-terminal Vitronectin. The method of producing brain microvascular endothelium-like cells according to this item makes it possible to suppress a decrease in reproducibility upon induction of differentiation of pluripotent stem cells into brain microvascular endothelium-like cells, and to suppress variation in differentiation efficiency, so that the brain microvascular endothelium-like cells can be stably supplied.

(8) In the method of producing brain microvascular endothelium-like cells according to the above item, the pluripotent stem cells may be induced pluripotent stem cells.

(9) In the method of producing brain microvascular endothelium-like cells according to the above item, the induced pluripotent stem cells may be human induced pluripotent stem cells.

(10) Another aspect of the present invention provides a method for evaluating blood-brain barrier permeability of a test substance by using a cell layer of brain microvascular endothelium-like cells obtained by the method of producing brain microvascular endothelium-like cells according to the above item.

(11) The method for evaluating blood-brain barrier permeability of a test substance according to the above item may comprise the following steps (i) to (iii):

(i) preparing the cell layer;

(ii) bringing the test substance into contact with the cell layer; and (iii) evaluating permeability of the test substance by quantifying the test substance having permeated the cell layer.

(12) Another aspect of the present invention provides a method for evaluating an effect of a test substance on a blood-brain barrier function by using a cell layer of brain microvascular endothelium-like cells obtained by the method of producing brain microvascular endothelium-like cells according to the above item.

(13) Another aspect of the present invention provides a method of inducing differentiation of pluripotent stem cells into brain microvascular endothelium-like cells. The method of inducing differentiation of pluripotent stem cells into brain microvascular endothelium-like cells according to this item comprises a step of culturing the pluripotent stem cells while using at least one component of a Laminin-221 fragment or an N-terminal Vitronectin. The method of inducing differentiation of pluripotent stem cells into brain microvascular endothelium-like cells according to this item makes it possible to suppress a decrease in reproducibility upon induction of differentiation of pluripotent stem cells into brain microvascular endothelium-like cells, and to suppress variation in differentiation efficiency, so that the brain microvascular endothelium-like cells can be stably supplied.

DESCRIPTION OF EMBODIMENTS

Figure 1:
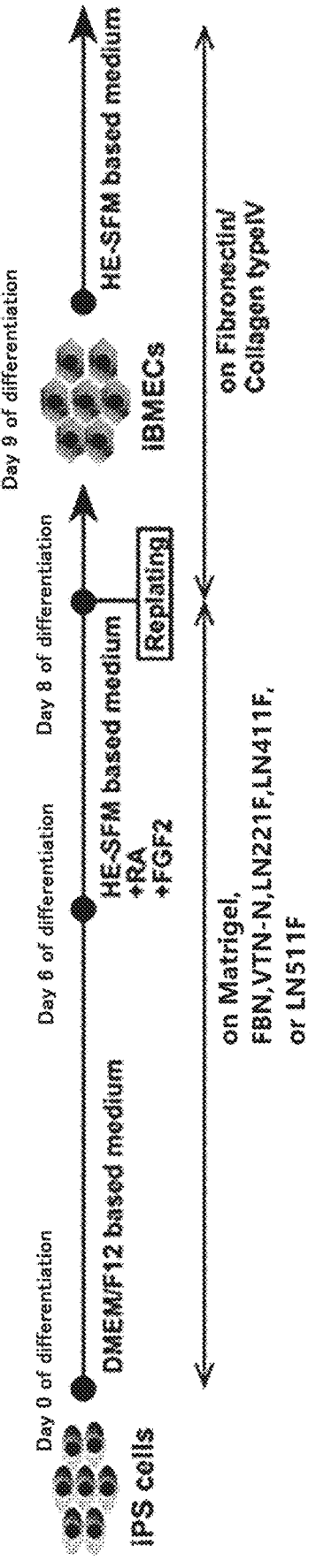
FIG. 1 is a scheme illustrating a protocol for differentiating human iPS cells into iBMECs.

The disclosure herein relates to a coating agent for inducing differentiation of pluripotent stem cells into brain microvascular endothelium-like cells. Brain microvascular endothelial cells (hereinafter, also referred to as "BMECs") are major cells constituting the blood-brain barrier (hereinafter, also referred to as "BBB"). The BBB has a structure in which BMECs are surrounded by and covered with pericytes and/or astrocytes. According to the present disclosure, cells similar to BMECs, that is, brain microvascular endothelium-like cells exhibiting characteristics of BMECs (hereinafter, also referred to as "iBMECs") can be obtained. The iBMECs obtained by the method of the present disclosure are useful for construction of a BBB model, and are used, for example, for evaluation of intra-brain transfer (blood-brain barrier permeability) of a test substance (typically, a drug).

The "pluripotent stem cell" refers to a cell having both the ability to differentiate into all cells constituting a living body (differentiation pluripotency) and the ability to produce daughter cells having the same differentiation potential as that of the self through replication (self-renewability). The differentiation pluripotency may be evaluated by transplanting cells to be evaluated into a nude mouse and by testing the presence or absence of formation of teratoma including respective cells from three germ layers (ectoderm, mesoderm, and endoderm).

Examples of the pluripotent stem cells include embryonic stem cells (ES cells), embryonic germ cells (EG cells), or induced pluripotent stem cells (iPS cells), but the pluripotent stem cells are not limited thereto as long as they are cells having both differentiation pluripotency and self-renewability. Preferably, ES cells or iPS cells are used. More preferably, iPS cells are used. The pluripotent stem cells are preferably mammalian (e.g., primates such as humans or chimpanzees, rodents such as mice or rats) cells, and particularly preferably human cells. Thus, in a most preferred embodiment of the present disclosure, human iPS cells are used as the pluripotent stem cells.

ES cells can be established, for example, by culturing an early embryo before implantation, an inner cell mass constituting the early embryo, or a single blastomere (Manipulating the Mouse Embryo A Laboratory Manual, Second Edition, Cold Spring Harbor Laboratory Press (1994); Thomson, J. A. et al., Science, 282, 1145-1147 (1998)). As the early embryo, an early embryo produced by nuclear transfer of a somatic cell nucleus may be used (Wilmut et al. (Nature, 385, 810 (1997)), Cibelli et al. (Science, 280, 1256 (1998)), Akira Iriya et al. ("Protein, Nucleic Acid, Enzyme", 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000)), Tachibana et al. (Human Embryonic Stem Cells Derived by Somatic Cell Nuclear Transfer, Cell (2013) in press)). Each parthenogenetic embryo may be used as the early embryo (Kim et al. (Science, 315, 482-486 (2007)), Nakajima et al. (Stem Cells, 25, 983-985 (2007)), Kim et al. (Cell Stem Cell, 1, 346-352 (2007)), Revazova et al. (Cloning Stem Cells, 9, 432-449 (2007)), Revazova et al. (Cloning Stem Cells, 10, 11-24 (2008))). Regarding the ES cell production, one can consult, in addition to the above research articles, for instance, Strelchenko N., et al. Reprod Biomed Online. 9: 623-629, 2004; Klimanskaya I., et al. Nature 444: 481-485, 2006; Chung Y., et al. Cell Stem Cell 2: 113-117, 2008; Zhang X., et al. Stem Cells 24: 2669-2676, 2006; and Wassarman, P. M. et al. Methods in Enzymology, Vol. 365, 2003. Note that each fused ES cell obtained by cell fusion of an ES cell and a somatic cell is also herein included in the embryonic stem cells.

Some ES cells are available from stock institutions or are commercially available. For example, human ES cells are available from, for instance, the Institute for Frontier Life and Medical Sciences, Kyoto University (e.g., KhES-1, KhES-2 and KhES-3), or WiCell Research Institute, ESI BIO. In addition, ES cells may be established by culturing primordial germ cells in the presence of LIF, bFGF, and SCF (Matsui et al., Cell, 70, 841-847 (1992), Shamblott et al., Proc. Natl. Acad. Sci. USA, 95 (23), 13726-13731 (1998), Turnpenny et al., Stem Cells, 21(5), 598-609, (2003)).

An iPS cell is a cell that can be produced through reprogramming of a somatic cell, for example, by introducing reprograming factors and has pluripotency (differentiation pluripotency) and proliferation potential. iPS cells exhibit characteristics close to those of ES cells. The somatic cell used for producing the iPS cell is not particularly limited, and may be a differentiated somatic cell or an undifferentiated stem cell. Also, the origin of the somatic cell is not particularly limited, and the somatic cell used is preferably a mammalian (e.g., primates such as humans or chimpanzees, rodents such as mice or rats) somatic cell, and particularly preferably a human somatic cell. The iPS cells can be produced by various methods reported so far. In addition, it is naturally presumed that iPS cell production methods to be developed in the future are also applicable.

The most basic technique for the iPS cell production methods is a method in which four factors Oct3/4, Sox2, Klf4, and c-Myc, which are transcription factors, are introduced into a cell by using viruses (Takahashi K, Yamanaka S: Cell 126 (4), 663-676, 2006; Takahashi, K, et al: Cell 131 (5), 861-72, 2007). Human iPS cells have been reportedly established by introduction of four factors Oct4, Sox2, Lin 28, and Nonog (Yu J, et al: Science 318 (5858), 1917-1920, 2007). Also, iPS cells have been reportedly established by introduction of three factors excluding c-Myc (Nakagawa M, et al: Nat. Biotechnol. 26 (1), 101-106, 2008), two factors of Oct3/4 and Klf4 (Kim J B, et al: Nature 454 (7204), 646-650, 2008), or only Oct 3/4 (Kim J B, et al: Cell 136 (3), 411-419, 2009). In addition, techniques for introducing each protein, which is an expression product of each gene, into a cell (Zhou H, Wu S, Joo J Y, et al: Cell Stem Cell 4, 381-384, 2009; Kim D, Kim C H, Moon J I, et al: Cell Stem Cell 4, 472-476, 2009) have also been reported. Meanwhile, it has also been reported that use of a histone methyl transferase G9a inhibitor (BIX-01294) or a histone deacetylase inhibitor (e.g., valproic acid (VPA) or Bay K 8644) makes it possible to improve the production efficiency and to decrease the number of factors to be introduced (Huangfu D, et al: Nat. Biotechnol. 26 (7), 795-797, 2008; Huangfu D, et al: Nat. Biotechnol. 26 (11), 1269-1275, 2008; Silva J, et al: PLoS. Biol. 6 (10), e253, 2008). The gene introduction procedure has also been studied, and other than the retrovirus, each technique using a lentivirus (Yu J, et al: Science 318(5858), 1917-1920, 2007), adenovirus (Stadtfeld M, et al: Science 322 (5903), 945-949, 2008), plasmid (Okita K, et al: Science 322 (5903), 949-953, 2008), transposon vector (Woltjen K, Michael I P, Mohseni P, et al: Nature 458, 766-770, 2009; Kaji K, Norrby K, Pac a, et al: Nature 458, 771-775, 2009; Yusa K, Rad R, Takeda J, et al: Nat Methods 6, 363-369, 2009), or episomal vector (Yu J, Hu K, Smuga-Otto K, Tian S, et al: Science 324, 797-801, 2009) for gene introduction has been developed.

It is possible to sort cells having been transformed into iPS cells, that is, reprogrammed cells by using, as indicators, expression of pluripotent stem cell markers (undifferentiated markers) such as Fbxo 15, Nanog, Oct/4, Fgf-4, Esg-1, and Cript. The sorted cells are collected as iPS cells.

Here, iPS cells may also be obtained, for example, from the National University Corporation Kyoto University or the National RIKEN BioResource Center.

As used herein, the wording "inducing differentiation" refers to making cells differentiate along a specific cell lineage(s). In the present disclosure, when pluripotent stem cells are induced and differentiated into brain microvascular endothelium-like cells (iBMECs), a coating agent containing at least one component of a Laminin-221 fragment (hereinafter, also referred to as "LN221F") or an N-terminal Vitronectin (hereinafter, also referred to as "VTN-N") is used. Hereinafter, details of the coating agent will be described.

<Coating Agent>

In general, cells may be cultured on a culture surface coated with, for instance, a basement membrane component(s) or an adhesion molecule(s) in order to improve cell viability or proliferation rate, promote differentiation induction, or select cells. Matrigel, which has been conventionally used as a coating agent, contains Laminin 111 as a main component, and further contains Collagen type IV, heparan sulfate proteoglycan, Entactin/Nidogen, and various growth factors.

Laminin is a heterotrimeric molecule consisting of three subunit chains including an α chain, a β chain, and a γ chain. Five types: α1 to α5 are known for the α chain, three types: β1 to β3 are known for the β chain, and three types: γ1 to γ3 are known for the γ chain. The following has been known as Reference Sequence RNA of Laminin, including NM_000426, NM_001079823 (Subunit alpha2), NM_002291 (Subunit beta1), NM_002292 (Subunit beta2), NM_000228 (Subunit beta3), NM_001318046, NM_001318047, NM_001318048, NM_007356 (Subunit beta4), NM_002293 (Subunit gamma 1), NM_005562, or NM_018891 (Subunit gamma 2).

Laminin 221 is a laminin molecule consisting of subunit chains including α2 chain, β2 chain, and γ1 chain, and is known to be abundant in the heart.

As used herein, the "Laminin-221 fragment (LN221F)" means a fragment (E8 fragment) corresponding to an Integrin binding site in Laminin-221. In addition, the "Laminin-221 fragment (LN221F)" herein also includes a protein having high homology to LN221F. As used herein, the "protein having high homology to LN221F" refers to a protein in which the amino acid sequence constituting the protein contains 80% or more identical amino acid sequence to the amino acid sequence of LN221F. That is, the "protein having high homology to LN221F" also includes a protein having an amino acid sequence longer than that of LN221F. From the viewpoint of enhancing the barrier function, the homology of a protein having high homology to LN221F is preferably 80% or more, more preferably 90% or more, and still more preferably 95% or more. In general, the molecular weight of the Laminin-221 fragment (LN221F) is from about 150 kDa to about 170 kDa. As used herein, the molecular weight of the Laminin-221 fragment (LN221F) is estimated to be 150 kDa.

As used herein, the term "N-terminal Vitronectin (VTN-N)" means a protein in which the N-terminal of vitronectin is deleted and which contains an RGD sequence. In addition, the "N-terminal Vitronectin (VTN-N)" herein also includes a protein having high homology to VTN-N. As used herein, the "protein having high homology to VTN-N" refers to a protein in which the amino acid sequence constituting the protein contains 70% or more identical amino acid sequence to the amino acid sequence of VTN-N or a protein containing an RGD sequence in the amino acid sequence. The "protein having high homology to VTN-N" also includes a protein having an amino acid sequence longer than that of VTN-N. From the viewpoint of enhancing the barrier function, the homology of a protein having high homology to VTN-N is preferably 80% or more, more preferably 90% or more, and still more preferably 95% or more. NM_000638 is known as Reference Sequence RNA of Vitronectin, and NNP_000629 is known as Reference Sequence protein of Vitronectin. As used herein, the molecular weight of the N-terminal Vitronectin (VTN-N) is estimated to be 47.6 kDa.

The coating agent of the present disclosure may contain only one of LN221F or VTN-N, or may contain both LN221F and VTN-N. That is, the coating agent of the present disclosure contains at least one component of LN221F or VTN-N. The coating agent of the present disclosure preferably contains LN221F. Note that Matrigel may be excluded from the coating agent of the present disclosure. The coating agent may contain the component in an amount of 0.01 nmol/L or more and 10 mmol/L or less. The content of the component in the coating agent is preferably 0.1 nmol/L or more and more preferably 1 nmol/L or more. The content of the component in the coating agent is preferably 1 mmol/L or less and more preferably 0.1 mmol/L or less. When the coating agent contains 0.01 nmol/L or more of the component, the differentiation efficiency can be improved. When the coating agent contains 1 mmol/L or less of the component, an increase in cost required for differentiation induction can be suppressed.

The coating agent containing the above component may be diluted with, for instance, a culture medium, and the mixture may be poured onto, for instance, a culture dish or a Transwell insert, and allowed to stand, so that the culture dish or the like on which a coating layer is formed can then be obtained. Hereinafter, forming the coating layer is also called "coating". The content of the component may be 1 ng or more and 1 mg or less per $cm^2$ of coating area of the coating layer, namely the area of the culture dish. The content of the component is preferably 10 ng or more and more preferably 0.1 μg or more per $cm^2$ of the coating area. In addition, the content of the component is preferably 0.1 mg or less and more preferably 10 μg or less per $cm^2$ of the coating area. When the component is contained in an amount of 1 ng or more per $cm^2$ of coating area of the coating layer, a decrease in differentiation efficiency can be further suppressed. In addition, when the component is contained in an amount of 1 mg or less per $cm^2$ of coating area of the coating layer, an increase in cost required for differentiation efficiency can be suppressed.

<Differentiation Induction Kit>

The coating agent in combination with cells to produce iBMECs may be provided in the form of a kit. That is, according to another embodiment of the present disclosure, there is provided a differentiation induction kit including the coating agent and cells. The cells used in this kit may be pluripotent stem cells as described above or intermediate cells in the process of differentiating pluripotent stem cells. Such pluripotent stem cells are preferably ES cells or iPS cells, and more preferably iPS cells. Meanwhile, such pluripotent stem cells to be used are preferably mammalian (e.g., primates such as humans or chimpanzees, rodents such as mice or rats) cells, and more preferably human cells. The intermediate cells in the differentiation process are preferably vascular endothelial progenitor cells. That is, the cells in this kit are particularly preferably vascular endothelial progenitor cells induced and differentiated from human iPS cells. In addition, the state of cells in this kit may be, for example, a state of being stored at 37° C. or a state of being cryopreserved. The cells in this kit are preferably frozen cells from the viewpoint of transportation and handling.

Each user of the kit can easily induce differentiation of cells into iBMECs by coating, for instance, a culture dish with a coating agent and then seeding and culturing cells thereon, or by seeding and culturing cells with the coating agent on, for instance, a culture dish. At the time of culture, (an)other material(s) may be used in combination with the coating agent and cells included in the kit, or subculture may be performed, if appropriate. Note that examples of the culture dish that can be used include a petri dish, a cell culture plate having a plurality of wells, or cultureware in any form.

LN221F or VTN-N is more easily handled than Matrigel because they are unlike Matrigel and are not solidified due to a temperature increase. In addition, the coating procedure is simple. Therefore, a decrease in reproducibility during differentiation induction can be suppressed. Further, LN221F or VTN-N is structured by a single component. This causes a small lot difference, thereby allowing to suppress variation in differentiation efficiency of iBMECs due to a difference in the manufacturing company and/or the production lot. Thus, the present disclosure makes it possible to stably supply iBMECs.

<Method of Producing iBMECs by Inducing Differentiation of Pluripotent Stem Cells>

The method of producing iBMECs by inducing differentiation of pluripotent stem cells in the present disclosure includes a step of culturing pluripotent stem cells while using at least one component of LN221F or VTN-N. This step may be a step of seeding pluripotent stem cells on, for instance, a culture dish coated with at least one component of LN221F or VTN-N at the time of subculture, and culturing the pluripotent stem cells in a culture medium.

Examples of a culture medium used and adopted for inducing differentiation include a basal medium such as DMEM Ham's F-12 (DMEM/F12) or Human Endothelial-SFM. It is preferable to add serum or a serum replacement (e.g., Knockout serum replacement (KSR)) to the culture medium from the viewpoint of the growth rate and maintenance of cells. The serum is not limited to fetal bovine serum, and human serum or sheep serum, for example, may also be used. In addition, plasma-derived serum (PDS) may be used instead of regular serum. The amount of serum or serum replacement added is, for example, from 0.1% (v/v) to 10% (v/v). It is preferable to add fibroblast growth factor (FGF) 2 such as human FGF2 (e.g., human recombinant FGF2) to the culture medium, and the concentration of FGF2 added may be, for example, from 1 ng/mL to 500 ng/mL.

The culture period for differentiation induction may be, for example, from 6 days to 30 days, and preferably from 8 days to 12 days. By setting the culture period accordingly, deterioration of the efficiency of inducing differentiation into iBMECs can be suppressed, and occurrence of unintended differentiation (differentiation into other cells) can also be suppressed.

Subculture may be performed in the middle of differentiation induction. For example, when the cells become confluent or sub-confluent, part of the cells may be collected and transferred to another cultureware. The culture may then be continued. At the time of cell recovery associated with, for instance, medium replacement or subculture, the cells may be treated in advance with a ROCK (Rho-associated coiled-coil forming kinase/Rho-binding kinase) inhibitor such as Y-27632 in order to suppress cell death. Also, to enhance the cell selection effect, cells may be seeded on a culture surface coated with Fibronectin and Collagen IV in the middle of differentiation induction.

Other culture conditions (e.g., culture temperature) may be conditions generally employed in the culture of animal cells. For example, the cells may be cultured under conditions at 37° C. and 5% $CO_2$. In addition, the method is not limited to the method of two-dimensionally culturing cells using, for instance, a culture dish, and three-dimensional culture may be performed using, for instance, a three-dimensional culture plate including a coating layer coated with the coating agent. Further, the present invention is not limited to an embodiment in which the coating agent is coated on cultureware such as a culture dish in advance, and an embodiment in which use of the coating agent and seeding of cells are simultaneously performed may be employed.

The above-described differentiation-inducing method may be used to produce iBMECs from pluripotent stem cells. A monolayer (cell layer) of iBMECs is formed by subsequent culture under culture conditions suitable for maintenance and proliferation of iBMECs. According to the method of the present disclosure, a cell layer having an excellent barrier function is obtained. The barrier function of the cell layer obtained by the method of the present disclosure can be characterized by strong tight junctions and maintenance of the tight junctions for a long period of time.

Here, it is generally known that BMECs in a rat in vivo have a transendothelial electrical resistance value (TEER value), which is an index of tight junction, of about 1000 to $2000\Omega \times cm^2$, and as a model of human BBB, it is desirable to have a TEER value of $1000\Omega \times cm^2$ or higher.

According to the method of producing iBMECs in the present embodiment, a cell layer having a TEER value of $1000\Omega \times cm^2$ or higher can be formed, and a TEER value exceeding $1000\Omega \times cm^2$ can be maintained for a long period of time, for example, 9 days or longer.

The barrier function of the cell layer obtained by the method of the present disclosure can also be further characterized by having a function of important or characteristic drug transporter (e.g., BCRP, P-gp, GLUT1) in the BMEC. In addition, the function of iBMECs may be determined or evaluated using, as an indicator, expression of a tight junction marker (e.g., Claudin 5, Occludin, ZO-1) important or characteristic of BMEC.

At a later stage of differentiation induction, a cell layer of iBMECs can be formed on a semi-permeable membrane by culturing the cells on the semi-permeable membrane (porous membrane). This embodiment is particularly effective when the cell layer of iBMECs obtained by the production method of the present disclosure is used for various assays. For example, cultureware (e.g., Transwell (registered trademark), supplied by Corning Inc.) provided with a culture insert (having a culture surface composed of a semi-permeable membrane) can be used to culture cells in the insert to form a cell layer.

Another embodiment of the present disclosure relates to use of iBMECs produced by inducing differentiation by the method described above. As described above, according to the present disclosure, a cell layer composed of iBMECs can be obtained, and the cell layer can be used for a BBB model. For example, an assay using the cell layer is useful for evaluating the BBB permeability of a test substance such as a pharmaceutical product or a pharmaceutical candidate. Here, the cell layer of iBMECs obtained by the production method of the present disclosure may be used to provide a method for evaluating test substance BBB permeability (hereinafter, also referred to as "BBB permeability evaluation method of the present disclosure"). The BBB permeability evaluation method of the present disclosure includes the following steps (i) to (iii):
  (i) preparing a cell layer of iBMECs obtained by the production method of the present disclosure;
  (ii) bringing a test substance into contact with the cell layer; and
  (iii) evaluating permeability of the test substance by quantifying the test substance having permeated the cell layer.

In step (i), a cell layer of iBMECs obtained by the production method of the present disclosure is prepared. In addition to the cell layer of iBMECs, other cells (e.g., pericytes, astrocytes) may be used in combination. For example, cultureware having a culture insert may be used to form a cell layer of iBMECs in the culture insert (a cell layer is formed on a bottom upper surface of the culture insert); pericytes may be cultured in a state of being adhered to the bottom back surface of the culture insert (pericytes-adhered co-culture system), pericytes may be cultured in a section between the culture insert and each well (pericytes-non-adhered co-culture system), pericytes may be cultured in a state of being adhered to the bottom back surface of the culture insert and astrocytes may be cultured in a section between the culture insert and each well (pericytes-adhered/astrocytes-non-adhered co-culture system), or astrocytes may be cultured in a state of being adhered to the bottom back surface of the culture insert (astrocytes-adhered co-culture system), The "contact" in step (ii) is typically performed by adding a test substance to a culture medium. The timing of addition of the test substance is not particularly limited. Thus, after the culture in the test substance-free culture medium is started, the test substance may be added at a certain time point, or the culture may be started in a culture medium already containing the test substance.

Typically, a pharmaceutical product or a pharmaceutical candidate substance is used as the test substance. However, the test substance is not particularly limited, and organic compounds or inorganic compounds having various molecular sizes may each be used as the test substance. Examples of the organic compound include nucleic acid, peptide, protein, lipid (simple lipid, complex lipid (e.g., phosphoglyceride, sphingolipid, glycosylglyceride, cerebroside)), prostaglandin, isoprenoid, terpene, steroid, polyphenol, catechin, or vitamin (e.g., B1, B2, B3, B5, B6, B7, B9, B12, C, A, D, E). It is also possible to use, as the test substance, for example, plant extract, cell extract, or culture supernatant. Two or more kinds of test substances may be simultaneously added to investigate, for instance, interaction and/or synergy between the test substances. The test substance may be derived from a natural product or may be synthesized. In the latter case, for example, an efficient assay system may be constructed using a combinatorial synthesis technique.

The period during which the test substance is brought into contact may be optionally set. The contact period is, for example, from 10 minutes to 3 days and preferably from 1 hour to 1 day.

In step (iii), the test substance having permeated the cell layer is quantified. For example, in a case where cultureware having a culture insert such as Transwell (registered trademark) is used, the test substance having permeated through the culture insert, that is, the test substance having moved into the upper container (culture insert) or the lower container (well) through the cell layer is quantified by an assay protocol corresponding to the test substance. Examples of the assay protocol include an assay protocol such as mass spectrometry, liquid chromatography, or immunological technique (e.g., fluorescent immunoassay (FIA), enzyme immunoassay (EIA)). The membrane permeability of the test substance is evaluated based on the quantification results (the amount of test substance having permeated the cell layer) and the amount of test substance used (typically, the amount added to the culture medium). In addition to the membrane permeability, for instance, absorption by the cell layer (absorbability), the effect on the cell layer (e.g., the effect on the barrier function), and/or the effect on the expression or function of a transporter (e.g., BCRP or P-gp) may be evaluated. Usually, the absorbability and the permeability have a front-back relation. Thus, they may be evaluated by the same method as in the case of permeability. The effect on the barrier function may be evaluated, for example, by measuring the TEER value or conducting a permeability test using a non-absorbable marker. In addition, the effect on the expression of a transporter may be evaluated by, for instance, an immunological technique, Western blotting, or flow cytometry, and the effect on the corresponding function may be evaluated, for example, by an activity test using a substrate.

As can be seen from the above description, the effect of the test substance on the BBB function (e.g., improvement, deterioration, and failure of the BBB function) may also be evaluated using the cell layer of iBMECs. Accordingly, as another application of the cell layer of iBMECs produced by the production method of the present disclosure, the present disclosure also provides a method for evaluating the BBB function as a target or subject, that is, a method for evaluating an effect of a test substance on the BBB function. This evaluation method is useful, for example, as a means for searching for a substance that enhances (improves) the barrier function, a substance that protects the barrier function, a substance that modulates the barrier function, and so on. The method may also be used for evaluation of toxicity to the BBB. In this evaluation method, like in the BBB permeability evaluation method, a step of preparing a cell layer and a step of bringing a test substance into contact with the cell layer are performed, and the effect on the barrier function of the cell layer is then evaluated. The procedure for evaluating the effect on the barrier function is as described above.

Examples

Hereinafter, the present invention will be described more specifically with reference to Examples. The present invention, however, is not limited to the following Examples. In the following description, unless otherwise specified, "%" indicates volume/volume %, and "w/v %" indicates weight/volume %. In addition, the materials used in Examples were obtained from the companies designated in Table 1.

TABLE 1

| Reagent name | Company name |
| --- | --- |
| Matrigel GFR | Corning Incorporated |
| FBN | Wako Pure Chemical Industries |
| VTN-N | Thermo Fisher Scientific |
| LN221F | Nippi Incorporated |
| LN411F | |
| LN511F | |
| StemSure hPSC medium | Wako Pure Chemical Industries |
| L-Glu | |
| DMEM/F12 | |
| NEAA | |

TABLE 1-continued

| Reagent name | Company name |
| --- | --- |
| 2-MeE | Sigma-Aldrich Corporation |
| FBS | |
| HEPES | |
| KSR | Thermo Fisher Scientific |
| HBSS | |
| Human Endothelial-SFM | |
| FGF2 | PeproTech, Inc. |
| Penicillin-Streptomycin | Biological Industries USA, Inc. |
| Agencourt RNAdvance Tissue Total RNA Purification Kit | Beckman Coulter, Inc. |
| ReverTra Ace ® qPCR RT Master Mix | Toyobo Co., Ltd. |
| KAPA SYBR ® FAST qPCR Master Mix (2×) | Nippon Genetics Co. , Ltd. |
| PDS | Alfa Aesar |
| All-trans retinoic acid | Tocris Bioscience |
| Accutase | Nacalai Tesque, Inc. |
| DAPI | Dojindo |
| Collagen type IV | Nitta Gelatin Inc. |
| Human-derived primary BMECs (RNA) | ScienCell Research Laboratories, Inc. |
| Human-derived iPS cell lines 610B1, 648A1 | RIKEN BioResource Center |

1. Materials and Methods (1) Medium

Mouse embryonic fibroblasts (MEFs) as feeder cells were cultured using Dulbecco's Modified Eagle's Medium (DMEM) containing 10% fetal bovine serum (FBS), 2 mmol/L L-glutamine (L-Glu), 1% non-essential amino acids (NEAA), and 1× penicillin-streptomycin. MEF stripping solution used was 0.05 w/v % trypsin-ethylenediaminetetraacetic acid (EDTA), and MEF preservation solution used was Cell Banker 1. Human iPS cells were maintained and cultured using DMEM Ham's F-12 (DMEM/F12) containing 20% KnockOut Serum Replacement (KSR), 0.8% NEAA, 2 mmol/L L-Glu, 0.1 mmol/L 2-mercaptoethanol (2-MeE), and 5 ng/mL fibroblast growth factor (FGF) 2. Human iPS cell stripping solution used was Dulbecco's phosphate buffered saline (PBS) containing 1 mg/mL collagenase IV, 0.25 w/v % trypsin, 20% KSR, and 1 mmol/L calcium chloride. Human iPS cell preservation solution used was Cell Reservoir 1.

(2) To Culture Human iPS Cells

Human iPS cells used were 610B1 strain or 648A1 strain (each obtained from RIKEN). Human iPS cells were seeded on MEF ($6\times10^5$ cells/100 mm dish) treated with mitomycin C, and cultured at 37° C. in a $CO_2$ incubator under 5% $CO_2$/95% air conditions. The human iPS cells were subcultured at a split ratio of 1:2 to 1:4 after culturing for 3 to 5 days.

(3) Coating Agent

Matrigel GFR (Growth Factor Reduced), Fibronectin (hereinafter also referred to as "FBN"), N-terminal Vitronectin (hereinafter also referred to as "VTN-N"), Laminin 221 fragment (hereinafter also referred to as "LN221F"), Laminin 411 fragment (hereinafter also referred to as "LN411F"), and Laminin 511 fragment (hereinafter also referred to as "LN511F") were each used as a coating agent at the start of inducing differentiation. In addition, a mixture of Fibronectin and Collagen type IV was used as a coating agent during subculture in the middle of differentiation induction. In the following description, Matrigel GFR is also simply referred to as "Matrigel". Note that the concentration of the LN221F-containing coating agent was 175 µg/0.35 mL, and the concentration of the VTN-N-containing coating agent was 0.5 mg/mL.

(4) To Form Coating Layer

A coating layer was formed using each of the above-described coating agents. Matrigel was diluted 30-fold with a maintenance medium for human iPS cells on ice, poured onto a well plate, and allowed to stand at 37° C. for 30 minutes or longer to form a coating layer. FBN, VTN-N, LN221F, LN411F, or LN511F was diluted with PBS so as to be 1 μg/cm², poured onto a well plate, and allowed to stand at 37° C. for 1 hour to 2 hours to form a coating layer. In addition, a mixture of Fibronectin and Collagen type IV was diluted with PBS so as to be 100 μg/mL and 400 μg/mL, respectively, poured onto a Transwell insert, and allowed to stand at 37° C. for 2 hours or longer to form a coating layer.

(5) To Induce Differentiation of Human iPS Cells into iBMECs

FIG. 1 is a scheme illustrating a protocol for differentiating human iPS cells into iBMECs. As shown in FIG. 1, when human iPS cells were induced and differentiated into iBMECs, Matrigel or each single basement membrane component as described above was used as a coating agent from day 0 to day 8 of differentiation of iBMECs. The differentiation induction was started in a state in which at the time of passage, the cells were seeded on a culture dish coated with each coating agent and cultured in StemSure hPSC medium containing 35 μg/mL FGF2 until the proportion of undifferentiated colonies reached about 60 to 70% (day 0 of differentiation). The cells were cultured (until day 6 of differentiation) for 6 days using DMEM/F12-based medium prepared by adding 20% KSR, 0.8% NEAA, 2 mmol/L L-Glu, and 0.1 mmol/L 2-MeE to DMEM/F12, and then cultured for 2 days in a medium in which 10 μM all-trans retinoic acid (RA) and 20 ng/mL FGF2 were added to HE-SFM based medium, namely Human Endothelial-SFM (HE-SFM) containing 1% platelet-poor plasma derived serum (PDS) and 1× penicillin-streptomycin. Thereafter (on day 8 of differentiation), the cells were detached with Accutase and seeded at $3 \times 10^5$ cells/well onto a Transwell insert or a culture dish coated with Fibronectin and Collagen type IV. The cells were cultured for 1 day in HE-SFM based medium containing 10 μM RA and 20 ng/mL FGF2 (until day 9 of differentiation), and then cultured in HE-SFM based medium (free of RA and FGF2) to induce differentiation into iBMECs. Medium was not changed after day 9 of differentiation.

(6) To Measure Transendothelial Electrical Resistance (TEER) Value

TEER values of iBMECs (on day 10 of differentiation) derived from 610B1 strain, which cells had been induced and differentiated on Matrigel or FBN, VTN-N, LN221F, LN411F, or LN511F, were measured. The number of samples was 3, and relative TEER values of iBMECs induced and differentiated on FBN, VTN-N, LN221F, LN411F, or LN511F were determined based on the TEER values of iBMECs induced and differentiated on Matrigel (hereinafter, also referred to as "Matrigel-iBMECs"). In addition, for each of 610B1 strain or 648A1 strain, the TEER values of Matrigel-iBMECs or iBMECs induced and differentiated on LN221F (hereinafter, also referred to as "LN221F-iBMECs") were measured from day 1 after seeding (day 9 of differentiation) to day 10 after seeding (day 18 of differentiation). The number of samples was set to 6, and the time-course change of the TEER values was determined. The TEER values were measured using a Millicell ERS-2 (chopstick type) according to the attached instructions. The volume of culture medium was 300 μL on the apical side and 800 μL on the basal side.

(7) Test for Permeability of Fluorescein Isothiocyanate-Dextran 4 kDa (FD4) or Lucifer Yellow (LY)

FD4 or LY permeability was tested on Matrigel-iBMECs and LN221F-iBMECs derived from each of 610B1 or 648A1 strain. The number of samples was 6. On day 10 of differentiation, the culture medium was replaced with a transport buffer (HBSS containing 10 mM HEPES solution), and the cells were cultured at 37° C. for 20 minutes. The transport buffer containing 1 mg/mL FD4 or 300 μM LY was added to the apical side. After incubation at 37° C. for 60 minutes, 100 μL of the solution was collected from the basolateral side. The volume of transport buffer was 300 μL on the apical side and 800 μL on the basal side. The fluorescence intensity of FD4 or LY was measured with a Synergy HTX multimode plate reader and analyzed by Gen5 data analysis software.

(8) RNA Extraction

Extraction was performed according to the attached instructions of Agencourt (registered trademark) RNAdvance Tissue Kit.

(9) Reverse Transcription Reaction

Complementary DNA (cDNA) was synthesized using ReverTra Ace (registered trademark) qPCR RT Master Mix according to the attached instructions.

(10) RT-q PCR Protocol

The levels of gene expression in Matrigel-iBMECs or LN221F-iBMECs derived from strain 610B1 (on day 10 of differentiation) or human-derived primary BMECs (hereinafter, also referred to as "hBMECs") were analyzed by RT-q PCR. The number of samples for Matrigel-iBMECs or LN221F-iBMECs was 3, and the number of samples for hBMECs was 1. RT-q PCR was performed with KAPA SYBR Fast qPCR Kit while using cDNA as a template according to the attached instructions. The primer sequences used in RT-q PCR are shown in Table 2. The results obtained were corrected using HPRT1 as an internal control. The relative expression levels of mRNA in LN221F-iBMECs or hBMECs were determined based on the expression levels of mRNA in Matrigel-iBMECs. Note that primers used in the RT-q PCR are as follows: the sequence of CDH5 forward primer is set forth in SEQ ID NO: 1; the sequence of CDH5 reverse primer is set forth in SEQ ID NO: 2; the sequence of MDR1 forward primer is set forth in SEQ ID NO: 3; the sequence of MDR1 reverse primer is set forth in SEQ ID NO: 4; the sequence of BCRP forward primer is set forth in SEQ ID NO: 5; the sequence of BCRP reverse primer is set forth in SEQ ID NO: 6; the sequence of GLUT1 forward primer is set forth in SEQ ID NO: 7; the sequence of GLUT1 reverse primer is set forth in SEQ ID NO: 8; the sequence of Occludin forward primer is set forth in SEQ ID NO: 9; the sequence of Occludin reverse primer is set forth in SEQ ID NO: 10; the sequence of ZO-1 forward primer is set forth in SEQ ID NO: 11; the sequence of ZO-1 reverse primer is set forth in SEQ ID NO: 12; the sequence of LAT1 forward primer is set forth in SEQ ID NO: 13; the sequence of LAT1 reverse primer is set forth in SEQ ID NO: 14; the sequence of HPRT1 forward primer is set forth in SEQ ID NO: 15; and the sequence of HPRT1 reverse primer is set forth in SEQ ID NO: 16.

TABLE 2

| Genes | Forward primer sequence (5'→3') | Reverse primer sequence (5'→3') |
| --- | --- | --- |
| CDH5 | GATTTGGAACCAGATGCACA | ACTTGGCATTCTTGCGACTC |
| MDRI | CCCATCATTGCAATAGCAGG | TGTTCAAACTTCTGCTCCTGA |
| BCRP | AGATGGGTTTCCAAGCGTTCAT | CCAGTCCCAGTACGACTGTGACA |
| GLUTI | GAAGAGAGTCGGCAGATGATG | GGAGTAATAGAAGACAGCGTTGATG |
| Occludin | TCCAATGGCAAAGTGAATGA | GCAGGTGCTCTTTTTGAAGG |
| ZO-1 | CGAGGGATAGAAGTGCAAGTAGA | TATTCTTCATTTTTCCGGGATTT |
| LATI | AATGGGTCCCTGTTCACATC | CGTAGAGCAGCGTCATCACA |
| HPRTI | CTTTGCTTTCCTTGGTCAGG | TCAAGGGCATATCCTACAACA |

(11) Immunostaining

Matrigel-iBMECs or LN221F-iBMECs (on day 10 of differentiation) derived from 610B1 strain were analyzed by immunostaining in order to analyze the expression levels and localizations of BMEC marker proteins. The antibodies used in the immunostaining are shown in Table 3. For Zonula Occludens-1 (ZO-1) and Occludin, the cells on a 96-well plate were fixed in 4 w/v % paraformaldehyde for 15 minutes at room temperature, washed twice with glycine-containing PBS, and then permeabilized with 0.1 w/v % Triton X-100-containing PBS for 25 minutes at room temperature. After blocking for 20 min at room temperature with 5% donkey serum, each primary antibody was used for reaction for 2 hours at room temperature. After washed three times with PBS, the cells were reacted with the secondary antibody, which had been diluted 200-fold, for 60 minutes at room temperature. At this time, 1 μg/mL DAPI as a nuclear staining reagent was mixed in the reaction at the same time. Thereafter, the cells were washed three times with PBS, and were analyzed with an Operetta high content imaging system. Regarding Cadherin 5 (CDH5), Claudin 5, P-glycoprotein (P-gp), and breast cancer resistant protein (BCRP), the cells on a 96-well plate were washed 3 times with D-PBS (–) containing 0.1 w/v % BSA, then fixed in 4 w/v % paraformaldehyde for 15 minutes, washed again 3 times with PBS containing 0.1 w/v % BSA, and then permeabilized with PBS containing 0.1 w/v % Triton X-100 for 5 minutes. Subsequently, after washed 3 times with PBS containing 0.1 w/v % BSA, the cells were reacted with each primary antibody overnight at 4° C. Thereafter, the cells were washed three times with PBS containing 0.1 w/v % BSA, and reacted with a secondary antibody (anti-rabbit or anti-mouse one), which had been diluted 200-fold, for 60 minutes at room temperature. The cells were then washed 3 times with PBS containing 0.1 w/v % BSA, and reacted with 1 μg/mL DAPI for 5 minutes. After that, the cells were reacted in 4 w/v % paraformaldehyde for 5 minutes. Subsequently, the cells were washed three times with PBS, followed by analysis with an Operetta high content imaging system.

TABLE 3

| Targets | Manufacturer | Catalog number | Species | Dilution |
| --- | --- | --- | --- | --- |
| CDH5 | Santa Cruz | sc-9989 | Mouse | 1:25 |
| P-gp | Abcam | ab10333 | Mouse | 1:25 |
| BCRP | Abcam | ab3380 | Mouse | 1:50 |

TABLE 3-continued

| Targets | Manufacturer | Catalog number | Species | Dilution |
| --- | --- | --- | --- | --- |
| Oceludin | Fisher Scientific | 71-1500 | Rabbit | 1:50 |
| ZO-1 | Fisher Scientific | 33-9100 | Mouse | 1:100 |
| Claudin-5 | Fisher Scientific | 35-2500 | Mouse | 1:50 |
| Anti-abbit (Alexa Flour 488) | Fisher Scientific | A-21206 | Donkey | 1:200 |
| Anti-Mouse (Alexa Fluor 568) | Fisher Scientific | A-11004 | Goat | 1:200 |

(12) To Analyze Functions of P-Gp and BCRP

For functional analysis of P-gp and BCRP as efflux transporters, Matrigel-iBMECs or LN221F-iBMECs (on day 10 of differentiation) derived from 610B1 strain were tested for substrate uptake. As the substrate, rhodamine 123 or Hoechst 33342 was used. The culture medium was removed and the cells on a 96-well plate were pre-incubated in a transport buffer for 15 minutes at 37° C. Note that the number of samples was 6. The cells were incubated, in the presence or absence of 10 μM cyclosporine A (CsA), an inhibitor of P-gp, or 20 μM Ko 143, an inhibitor of BCRP, in a transport buffer containing 10 μM rhodamine 123 or 10 μM Hoechst 33342 for 60 minutes at 37° C. The cells were then washed three times with PBS and lysed in PBS containing 5 w/v % Triton X-100. The fluorescence intensities of rhodamine 123 or Hoechst 33342 were measured with a Synergy HTX multimode plate reader and analyzed by Gen5 data analysis software.

2. Results and Discussion (1) Relative TEER Values Based on Matrigel-iBMECs

Figure 2:
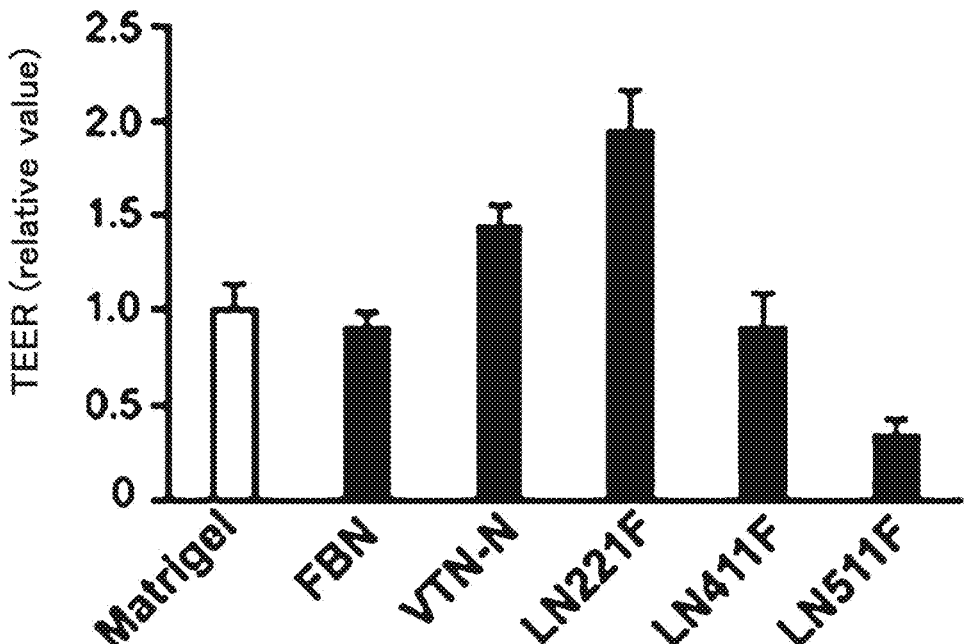
FIG. 2 is a graph showing relative TEER values of iBMECs induced and differentiated on each coating layer.

FIG. 2 is a graph showing relative TEER values of iBMECs induced and differentiated on each coating layer. In FIG. 2, the ordinate represents the relative TEER value when the TEER value of Matrigel-iBMECs is set to 1.0 as a reference, and the abscissa represents the type of iBMECs. The results of FIG. 2 have demonstrated that iBMECs that had been induced and differentiated on LN221F or VTN-N exhibited a higher TEER value than iBMECs that had been induced and differentiated on Matrigel. In particular, LN221F-iBMECs showed a TEER value about 2 times higher than that of Matrigel-iBMECs. Therefore, it can be said that iBMECs induced and differentiated on LN221F or VTN-N have a higher barrier function than iBMECs induced and differentiated on Matrigel.

(2) Time-Course Change in TEER Values

Figure 3:
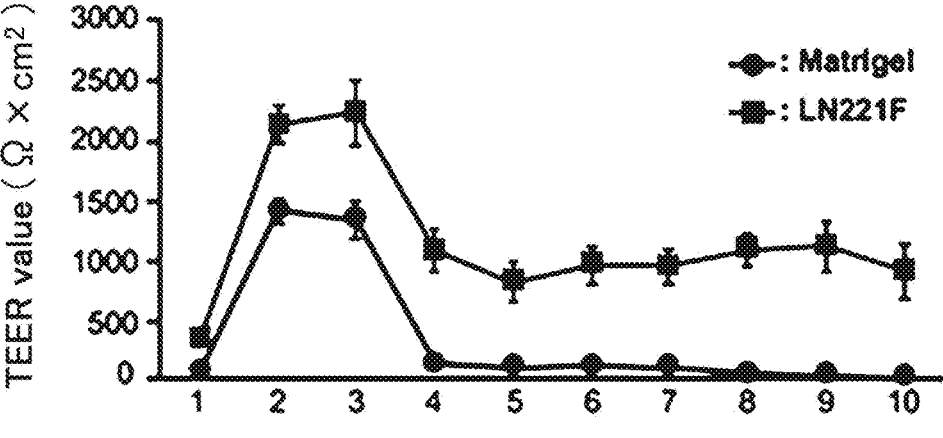
FIG. 3 is a graph indicating a time-course change in TEER values for Matrigel-iBMECs or LN221F-iBMECs derived from 610B1 strain.
Figure 4:
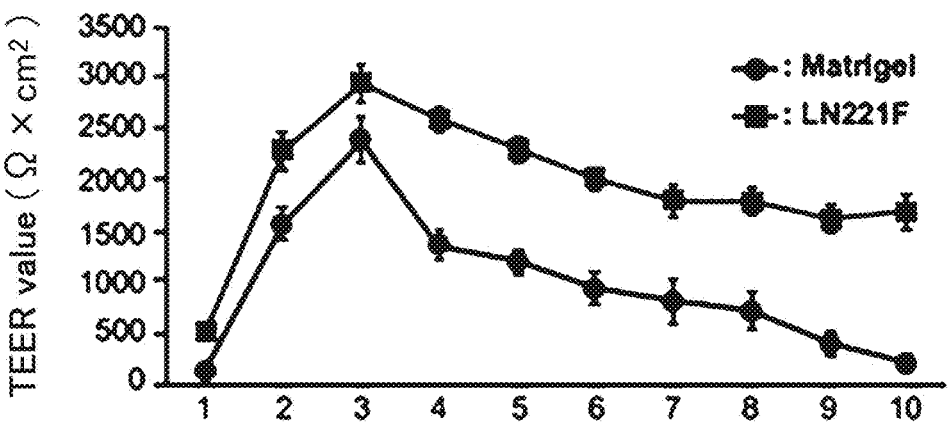
FIG. 4 is a graph indicating a time-course change in TEER values for Matrigel-iBMECs or LN221F-iBMECs derived from 648A1 strain.

FIG. 3 is a graph indicating a time-course change in TEER values for Matrigel-iBMECs or LN221F-iBMECs derived from 610B1 strain. FIG. 4 is a graph indicating a time-course change in TEER values for Matrigel-iBMECs or LN221F-iBMECs derived from 648A1 strain. In FIGS. 3 and 4, the ordinate represents the TEER value ($\Omega \times cm^2$), and the abscissa represents the number of days elapsed after seeding. The results shown in FIG. 3 and FIG. 4 have demonstrated that LN221F-iBMECs exhibited a higher TEER value than Matrigel-iBMECs over a long period of time regardless of whether 610B1 strain or 648A1 strain was used as human iPS cells. Therefore, it can be said that iBMECs induced and differentiated on LN221F have a higher barrier function over a long period of time than iBMECs induced and differentiated on Matrigel. In addition, it has been found that LN221F-iBMECs exhibited a TEER value of $1000\Omega \times cm^2$ or more over a long period of time in either case where 610B1 strain or 648A1 strain was used as human iPS cells, and are thus useful as a human BBB model.

(3) Permeability Test

Figure 5:
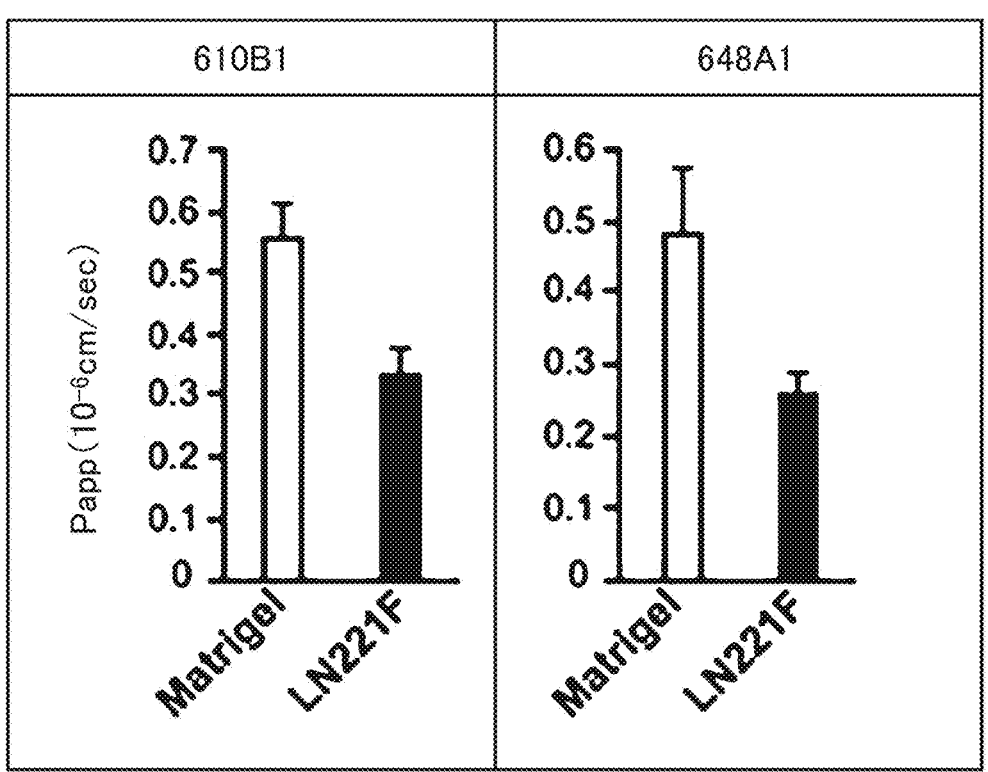
FIG. 5 is graphs showing the results of a test for permeability of FD4 in Matrigel-iBMECs or LN221F-iBMECs.
Figure 6:
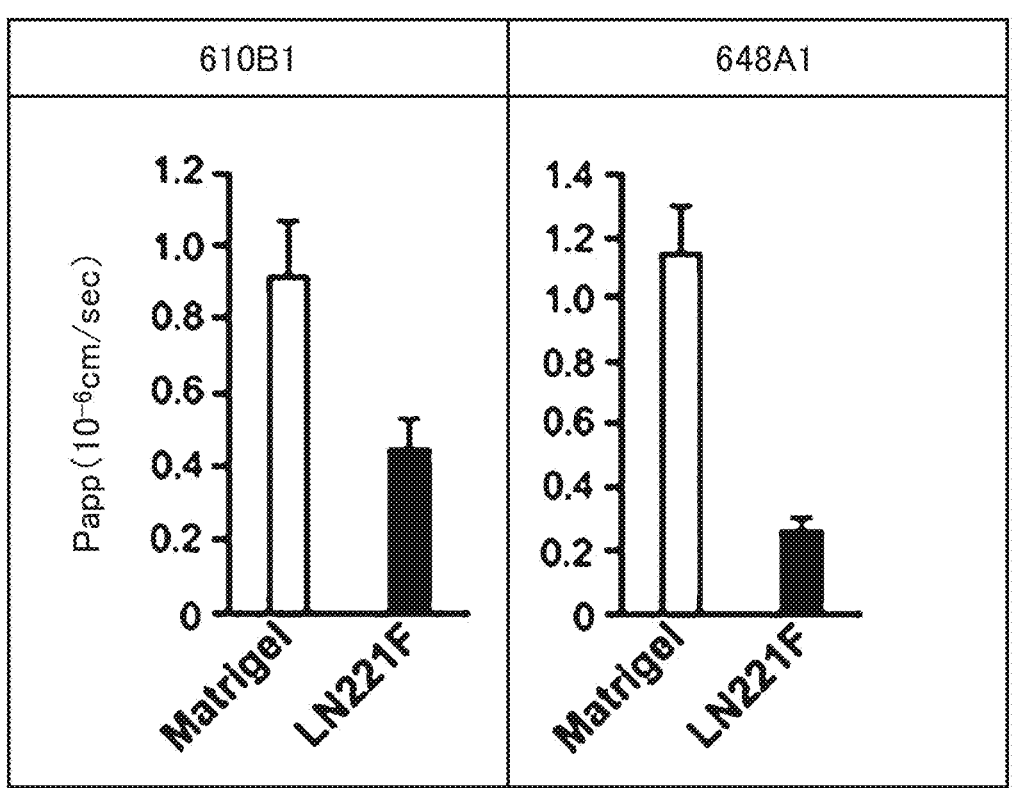
FIG. 6 is graphs showing the results of a test for permeability of LY in Matrigel-iBMECs or LN221F-iBMECs.

FIG. 5 is graphs showing the results of a test for permeability of FD4 in Matrigel-iBMECs or LN221F-iBMECs. FIG. 6 is graphs showing the results of a test for permeability of LY in Matrigel-iBMECs or LN221F-iBMECs. In FIGS. 5 and 6, the ordinate represents the permeability coefficient ($10^{-6}$ cm/sec), and the abscissa represents the type of iBMECs. The results shown in FIG. 5 and FIG. 6 have demonstrated that LN221F-iBMECs exhibited a lower permeability coefficient than Matrigel-iBMECs in either case where the 610B1 strain or the 648A1 strain was used as human iPS cells when FD4 and LY, which are indicators of permeability via the paracellular pathway, were each used as a permeant. It was found that high TEER values were exhibited over a long period of time. Therefore, it can be said that iBMECs induced and differentiated on LN221F have a higher barrier function than iBMECs induced and differentiated on Matrigel.

The results of the measurement of TEER values and the permeability tests have suggested that LN221F-iBMECs have a higher barrier function than Matrigel-iBMECs. Therefore, LN221F-iBMECs have been found to be useful as a human BBB model.

(4) Analysis of Expression Levels of Genes by RT-q PCR Protocol

Figure 7:
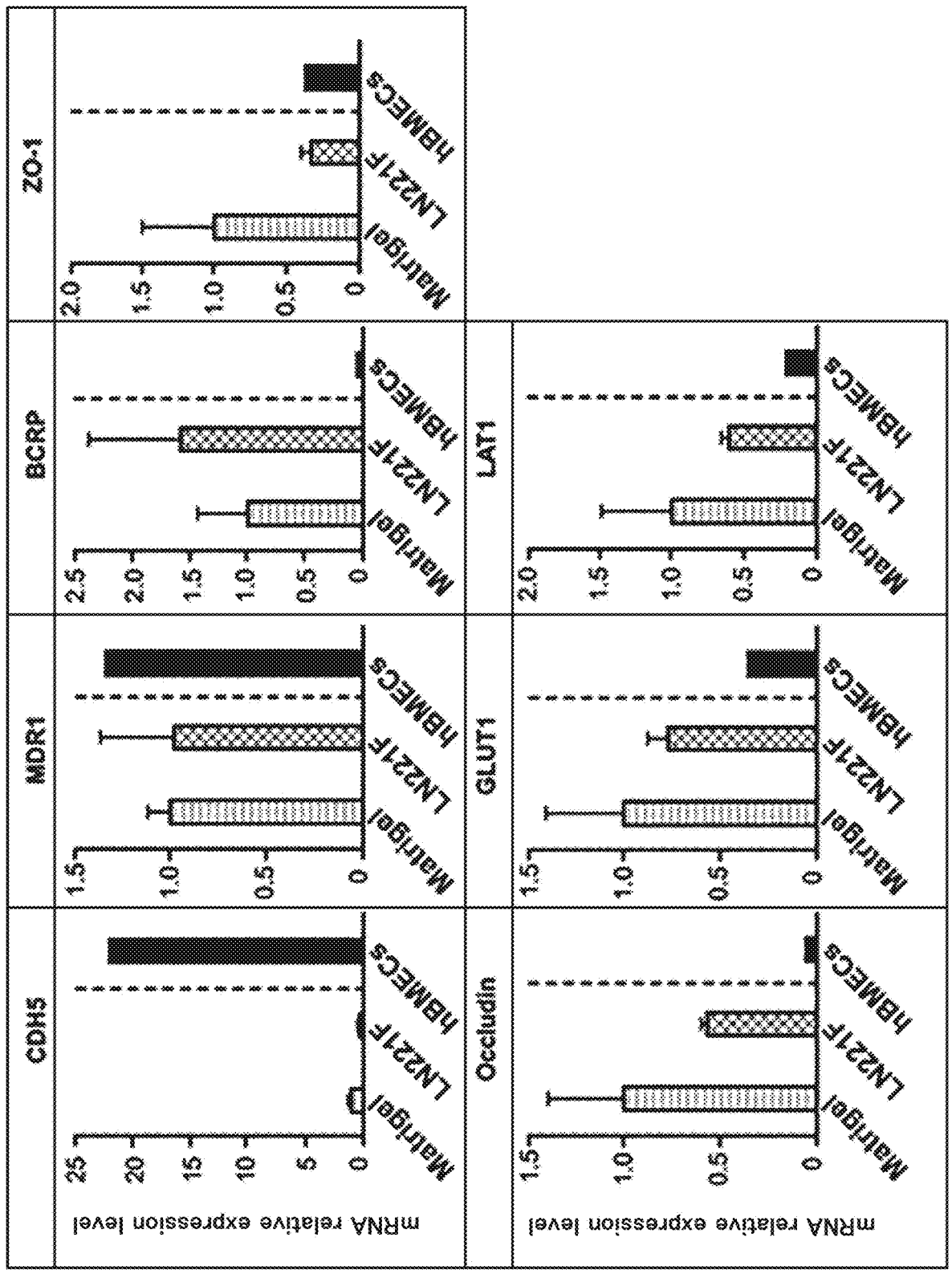
FIG. 7 is graphs showing the results of analyzing the expression levels of each gene in Matrigel-iBMECs, LN221F-iBMECs, or hBMECs.

FIG. 7 is graphs showing the results of analyzing the expression levels of each gene in Matrigel-iBMECs, LN221F-iBMECs, or hBMECs. In FIG. 7, the ordinate represents the relative mRNA expression levels when the expression level of each gene in Matrigel-iBMECs is set to 1.0 as a reference, and the abscissa represents the type of iBMECs or BMECs. The results shown in FIG. 7 have demonstrated that even when any of CDHS, MDR1, BCRP, ZO–1, Occludin, GLUT1, or LAT1 was used as a BMEC marker, LN221F-iBMECs exhibited an expression level almost equivalent to that of Matrigel-iBMECs.

(5) Study on Checking Protein Expression by Immunostaining

Figure 8:
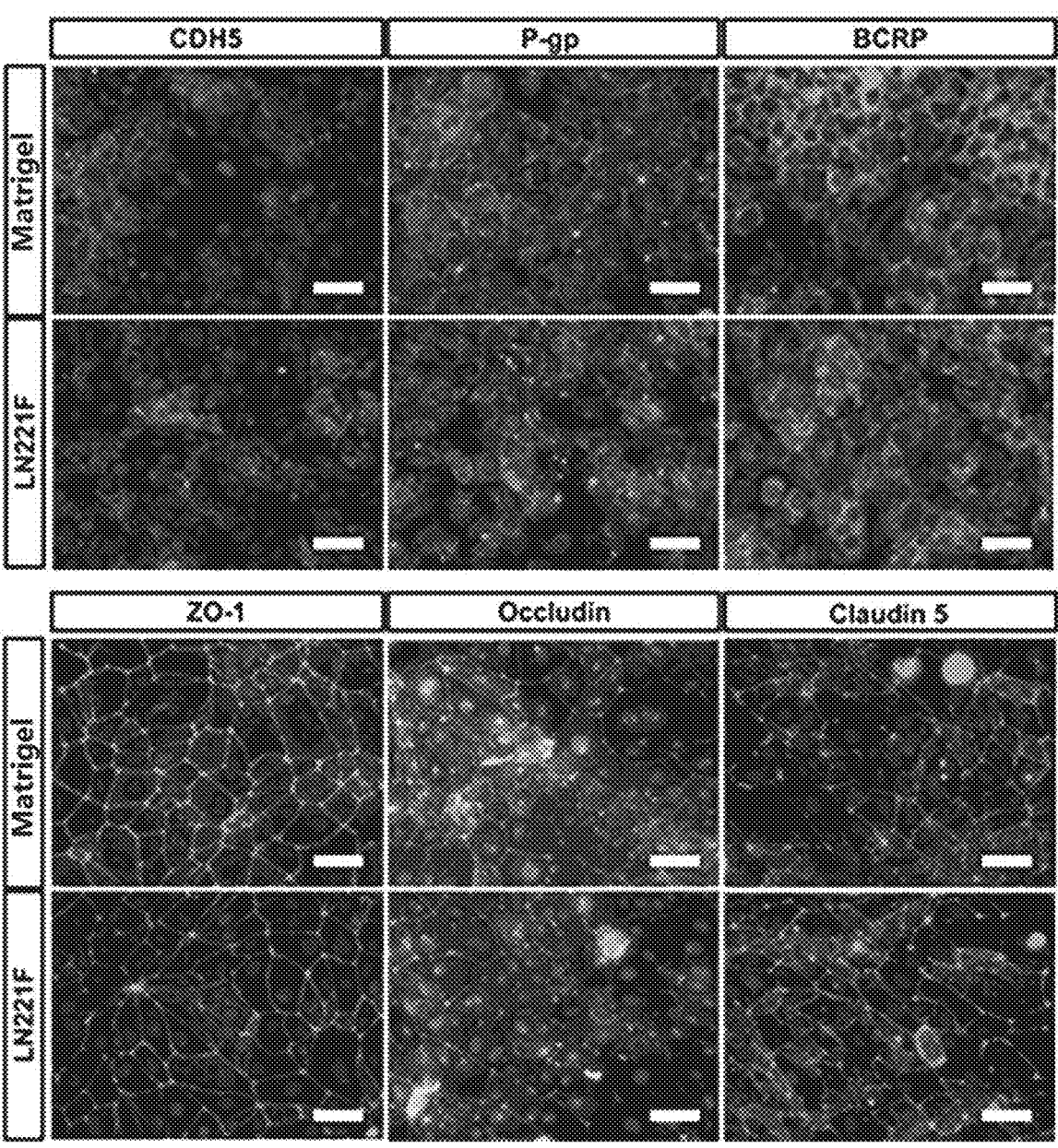
FIG. 8 is images showing the results of analyzing expression of each protein by immunostaining in Matrigel-iBMECs or LN221F-iBMECs.

FIG. 8 is images showing the results of analyzing expression of each protein by immunostaining in Matrigel-iBMECs or LN221F-iBMECs. In FIG. 8, a 50-μm scale bar is shown along with each image obtained by immunofluorescence staining. The results shown in FIG. 8 have demonstrated that even when any of CDH5, P-gp, BCRP, ZO-1, Occludin, or Claudin 5 was used as a BMEC marker, LN221F-iBMECs exhibited protein expression levels and localizations almost equivalent to those of Matrigel-iBMECs.

From the results of study on checking the gene expression and protein expression, it has been found that LN221F- iBMECs, like Matrigel-iBMECs, have characteristics as BMECs. Therefore, LN221F-iBMECs have been found to be useful as a human BBB model.

(6) Substrate Uptake Test

Figure 9:
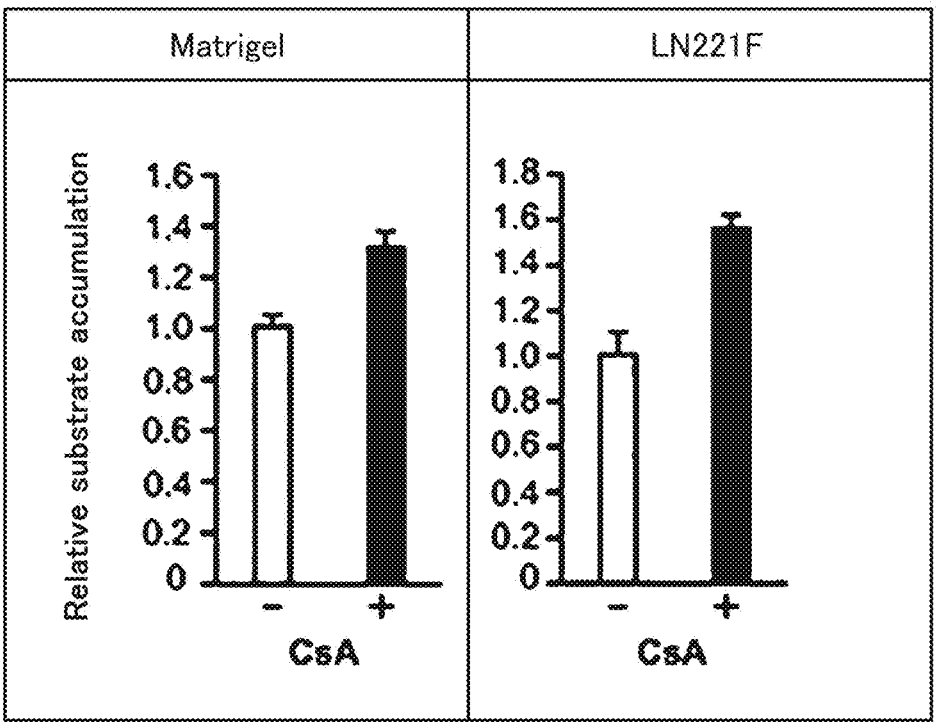
FIG. 9 is graphs showing the results of analyzing the P-gp function in Matrigel-iBMECs or LN221F-iBMECs.
Figure 10:
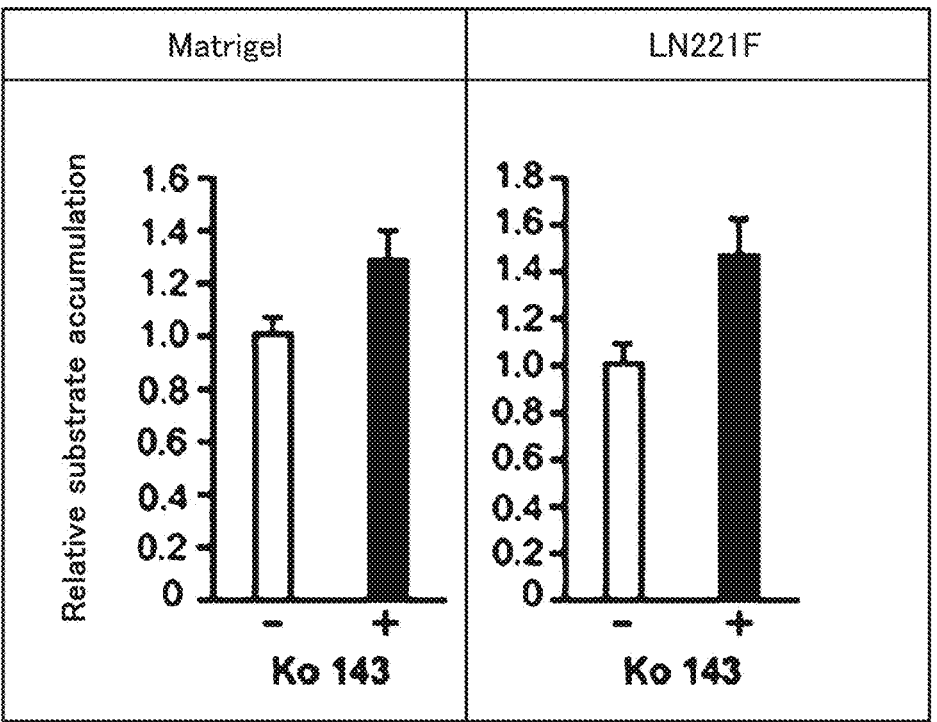
FIG. 10 is graphs showing the results of analyzing the BCRP function in Matrigel-iBMECs or LN221F-iBMECs.

FIG. 9 is graphs showing the results of analyzing the P-gp function in Matrigel-iBMECs or LN221F-iBMECs. FIG. 10 is graphs showing the results of analyzing the BCRP function in Matrigel-iBMECs or LN221F-iBMECs. In FIGS. 9 and 10, the ordinate represents the relative substrate accumulation when the substrate accumulation in the absence of an inhibitor for the efflux transporter is set to 1.0 as a reference, and the abscissa represents the presence or absence of the inhibitor for the efflux transporter. The results shown in FIG. 9 and FIG. 10 have verified that like in Matrigel-iBMECs, the accumulation of substrate in LN221F-iBMECs was larger in the presence of the inhibitor for the efflux transporter than in the absence of such an inhibitor. Therefore, it has been found that LN221F-iBMECs have P-gp and BCRP functions similar to those of Matrigel-iBMECs.

3. Conclusion

The above results have demonstrated that use of LN221F and/or VTN-N as a coating agent for iBMECs at the time of differentiation induction makes it possible to produce iBMECs having a higher barrier function than in the case of using Matrigel.

INDUSTRIAL APPLICABILITY

The present disclosure makes it possible to stably induce differentiation of pluripotent stem cells into iBMECs allowing for establishing a barrier function-enhanced BBB model. This enables stably supply of iBMECs and can contribute to the establishment of a system for supplying iBMECs to pharmaceutical companies and/or research institutions. Furthermore, the BBB model constructed using the present disclosure can be used for, for example, a system for evaluating efficacy/safety of some pharmaceutical product.

The present invention is not at all limited to the description of embodiments and examples of the invention. Various modifications that can be easily conceived by those skilled in the art without departing from the scope of the claims are also included in the present invention. The contents of the research articles, published patent application publications, patent publications, and others specified herein are incorporated by reference in their entirety.

SEQ ID NO: 1: Description of synthetic sequence: CDH5 forward primer

SEQ ID NO: 2: Description of synthetic sequence: CDH5 reverse primer

SEQ ID NO: 3: Description of synthetic sequence: MDR1 forward primer

SEQ ID NO: 4: Description of synthetic sequence: MDR1 reverse primer

SEQ ID NO: 5: Description of synthetic sequence: BCRP forward primer

SEQ ID NO: 6: Description of synthetic sequence: BCRP reverse primer

SEQ ID NO: 7: Description of synthetic sequence: GLUT1 forward primer

SEQ ID NO: 8: Description of synthetic sequence: GLUT1 reverse primer

SEQ ID NO: 9: Description of synthetic sequence: Occludin forward primer

SEQ ID NO: 10: Description of synthetic sequence: Occludin reverse primer

SEQ ID NO: 11: Description of synthetic sequence: ZO-1 forward primer

SEQ ID NO: 12: Description of synthetic sequence: ZO-1 reverse primer

SEQ ID NO: 13: Description of synthetic sequence: LAT1 5 forward primer

SEQ ID NO: 14: Description of synthetic sequence: LAT1 reverse primer

SEQ ID NO: 15: Description of synthetic sequence: HPRT1 forward primer

SEQ ID NO: 16: Description of synthetic sequence: HPRT1 reverse primer

The invention claimed is:

1. A method of producing brain microvascular endothelium cells by inducing differentiation of pluripotent stem cells, comprising a step of culturing the pluripotent stem cells on a culture surface that is coated with at least a Laminin-221 fragment.

2. The method of producing brain microvascular endothelium cells according to claim 1, wherein the pluripotent stem cells are induced pluripotent stem cells.

3. The method of producing brain microvascular endothelium cells according to claim 2, wherein the induced pluripotent stem cells are human induced pluripotent stem cells.

4. The method of producing brain microvascular endothelium cells according to claim 1, wherein the pluripotent stem cells are cultured on said culture surface that is coated with a Laminin-221 fragment at the initiation of differentiation induction.

* * * * *

```
                         SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: CDH5 forward primer

<400> SEQUENCE: 1
gatttggaac cagatgcaca                                        20

<210> SEQ ID NO 2
<211> LENGTH: 20
<212> TYPE: DNA
<213> ORGANISM: Artificial Sequence
<220> FEATURE:
<223> OTHER INFORMATION: CDH5 reverse primer

<400> SEQUENCE: 2
acttggcatt cttgcgactc                                        20

<210> SEQ ID NO 3
<211> LENGTH: 20
<212> TYPE: DNA
<213> ORGANISM: Artificial Sequence
<220> FEATURE:
<223> OTHER INFORMATION: MDR1 forward primer

<400> SEQUENCE: 3
cccatcattg caatagcagg                                        20

<210> SEQ ID NO 4
<211> LENGTH: 21
<212> TYPE: DNA
<213> ORGANISM: Artificial Sequence
<220> FEATURE:
<223> OTHER INFORMATION: MDR1 reverse primer

<400> SEQUENCE: 4
tgttcaaact tctgctcctg a                                      21

<210> SEQ ID NO 5
<211> LENGTH: 22
<212> TYPE: DNA
<213> ORGANISM: Artificial Sequence
<220> FEATURE:
<223> OTHER INFORMATION: BCRP forward primer

<400> SEQUENCE: 5
agatgggttt ccaagcgttc at                                     22

<210> SEQ ID NO 6
<211> LENGTH: 23
<212> TYPE: DNA
<213> ORGANISM: Artificial Sequence
<220> FEATURE:
<223> OTHER INFORMATION: BCRP reverse primer

<400> SEQUENCE: 6
```
ccagtcccag tacgactgtg aca                                             23

<210> SEQ ID NO 7
<211> LENGTH: 21
<212> TYPE: DNA
<213> ORGANISM: Artificial Sequence
<220> FEATURE:
<223> OTHER INFORMATION: GLUT1 forward primer

<400> SEQUENCE: 7
gaagagagtc ggcagatgat g                                               21

<210> SEQ ID NO 8
<211> LENGTH: 25
<212> TYPE: DNA
<213> ORGANISM: Artificial Sequence
<220> FEATURE:
<223> OTHER INFORMATION: GLUT1 reverse primer

<400> SEQUENCE: 8
ggagtaatag aagacagcgt tgatg                                           25

<210> SEQ ID NO 9
<211> LENGTH: 20
<212> TYPE: DNA
<213> ORGANISM: Artificial Sequence
<220> FEATURE:
<223> OTHER INFORMATION: Occludin forward primer

<400> SEQUENCE: 9
tccaatggca aagtgaatga                                                 20

<210> SEQ ID NO 10
<211> LENGTH: 20
<212> TYPE: DNA
<213> ORGANISM: Artificial Sequence
<220> FEATURE:
<223> OTHER INFORMATION: Occludin reverse primer

<400> SEQUENCE: 10
gcaggtgctc tttttgaagg                                                 20

<210> SEQ ID NO 11
<211> LENGTH: 23
<212> TYPE: DNA
<213> ORGANISM: Artificial Sequence
<220> FEATURE:
<223> OTHER INFORMATION: ZO-1 forward primer

<400> SEQUENCE: 11
cgagggatag aagtgcaagt aga                                             23

<210> SEQ ID NO 12
<211> LENGTH: 23
<212> TYPE: DNA
<213> ORGANISM: Artificial Sequence
<220> FEATURE:
<223> OTHER INFORMATION: ZO-1 reverse primer

<400> SEQUENCE: 12
tattcttcat ttttccggga ttt                                             23

<210> SEQ ID NO 13
<211> LENGTH: 20
<212> TYPE: DNA

-continued

```
<213> ORGANISM: Artificial Sequence
<220> FEATURE:
<223> OTHER INFORMATION: LAT1 forward primer

<400> SEQUENCE: 13
aatgggtccc tgttcacatc                                              20

<210> SEQ ID NO 14
<211> LENGTH: 20
<212> TYPE: DNA
<213> ORGANISM: Artificial Sequence
<220> FEATURE:
<223> OTHER INFORMATION: LAT1 reverse primer

<400> SEQUENCE: 14
cgtagagcag cgtcatcaca                                              20

<210> SEQ ID NO 15
<211> LENGTH: 20
<212> TYPE: DNA
<213> ORGANISM: Artificial Sequence
<220> FEATURE:
<223> OTHER INFORMATION: HPRT1 forward primer

<400> SEQUENCE: 15
ctttgctttc cttggtcagg                                              20

<210> SEQ ID NO 16
<211> LENGTH: 21
<212> TYPE: DNA
<213> ORGANISM: Artificial Sequence
<220> FEATURE:
<223> OTHER INFORMATION: HPRT1 reverse primer

<400> SEQUENCE: 16
tcaagggcat atcctacaac a                                            21
```